(12) United States Patent
Behan et al.

(10) Patent No.: US 7,824,715 B2
(45) Date of Patent: Nov. 2, 2010

(54) PERFUME COMPOSITIONS

(75) Inventors: John Martin Behan, Kent (GB); Keith Douglas Perring, Kent (GB); Les Small, Kent (GB); David McNulty, Kent (GB); Anne Richardson, Kent (GB)

(73) Assignee: Quest International B. V., Naarden (NL)

( * ) Notice: Subject to any disclaimer, the term of this patent is extended or adjusted under 35 U.S.C. 154(b) by 0 days.

(21) Appl. No.: 12/149,985

(22) Filed: May 12, 2008

(65) Prior Publication Data

US 2008/0255024 A1   Oct. 16, 2008

Related U.S. Application Data

(62) Division of application No. 10/450,900, filed as application No. PCT/GB01/05589 on Dec. 18, 2001, now abandoned.

(30) Foreign Application Priority Data

Dec. 20, 2000   (GB) ................... 0031047.4

(51) Int. Cl.
*A01N 65/00* (2009.01)
*A61F 13/00* (2006.01)
*A61K 36/00* (2006.01)

(52) U.S. Cl. ............... 424/725; 512/1; 512/8; 512/25; 424/443; 424/769

(58) Field of Classification Search ............ 512/1, 512/8, 25; 424/769, 443, 725
See application file for complete search history.

(56) References Cited

U.S. PATENT DOCUMENTS 4,671,959 A * 6/1987 Warren et al. ............. 424/769
4,929,599 A   5/1990 Giersch et al. ............. 512/18
5,374,614 A   12/1994 Behan et al. ............... 512/3
5,904,916 A   5/1999 Hirsch ........................ 424/45
6,268,333 B1  7/2001 Okazaki et al. ............. 512/20
6,399,811 B1  6/2002 Bajgrowicz et al. ......... 560/205
2002/0010107 A1  1/2002 Hoshino et al. ............. 510/101

FOREIGN PATENT DOCUMENTS

| DE | 41 25 562 A1 | 12/1992 |
| EP | 0 978 273 A1 | 2/2000 |
| WO | WO 99/44575 | 2/1999 |
| WO | WO 9944575 A1 * | 9/1999 |

OTHER PUBLICATIONS

Database WPI, Section Ch, Week 199806, Derwent Publications Ltd., XP-002189736, 19980059489.
Database WPI, Section Ch, Week 198839, Derwent Publications Ltd., XP-002189737, 1988-274031 [25].
Patent Abstracts of Japan, vol. 1998, No. 01, 09227399, Jan. 30, 1998.

* cited by examiner

*Primary Examiner*—Milton I Cano
*Assistant Examiner*—Aaron Greso
(74) *Attorney, Agent, or Firm*—Morgan Lewis & Bockius, LLP

(57) ABSTRACT

A perfume composition comprises: e) at least about 25% by weight in total of at least five selected relaxing fragrance materials (R); f) optionally up to about 45% by weight in total of non-relaxing fragrance materials (NR), provided that the ratio by weight of R to NR is at least 0.75; g) optionally up to about 75% by weight in total of neutral fragrance materials (N); h) optionally up to about 25% by weight of other fragrance materials (M) provided that the weight ratio R to (M+NR) at least 0.75; and wherein all percentages are based on total weight of the fragrance materials consisting the perfume composition.

1 Claim, 2 Drawing Sheets

PERFUME COMPOSITIONS

Figure 1:
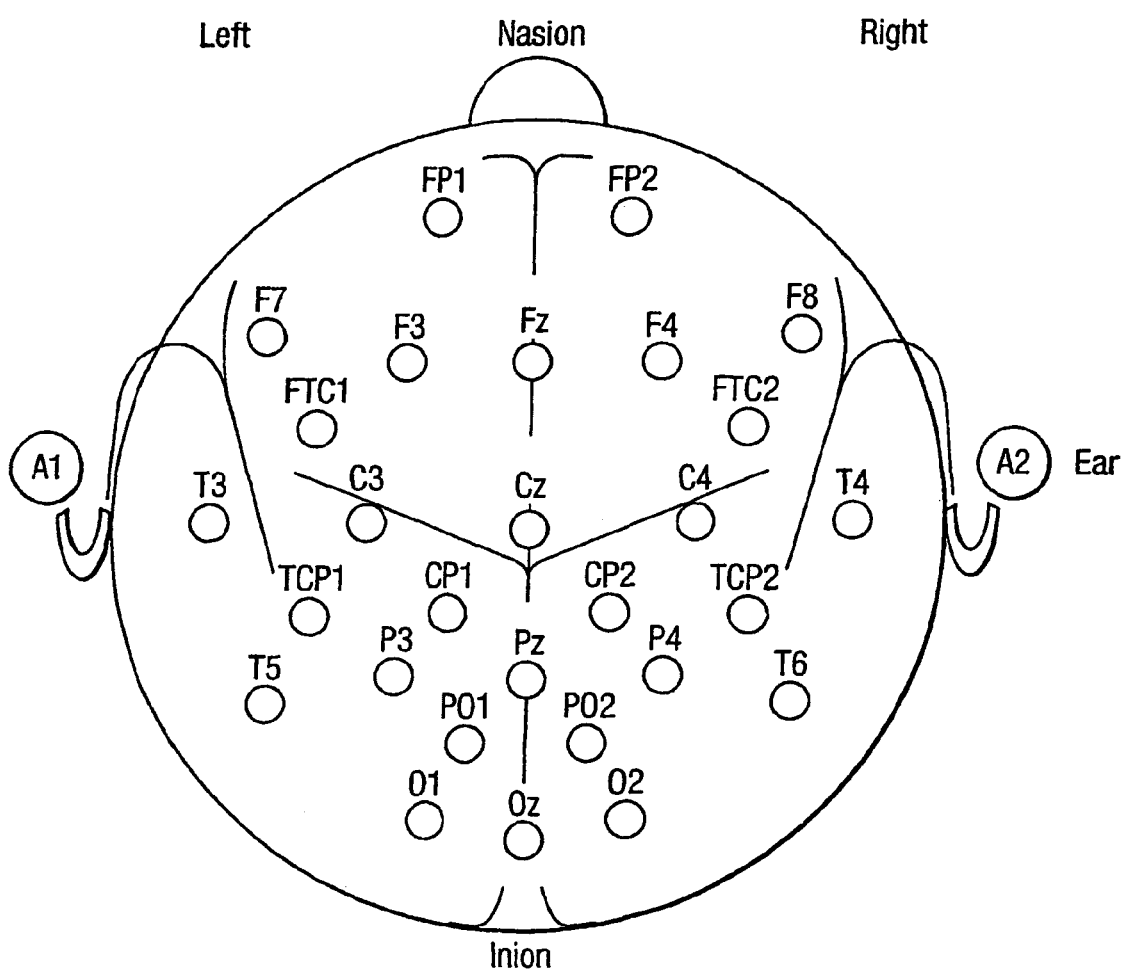

This application is a Divisional patent application under 37 C.F.R. §1.53(b), of pending prior application Ser. No. 10/450,900, filed on Nov. 3, 2003 now abandoned as a 371 of PCT/GB01/05589 filed Dec. 18, 2001, which claims priority to 0031047.4, filed Dec. 20, 2000.

FIELD OF THE INVENTION

This invention relates to perfume compositions which aim to promote relaxed and related mood states in subjects, particularly humans. The invention also concerns methods of delivering positive mood benefits or relaxation benefits to a subject.

BACKGROUND TO THE INVENTION

It has long been known that fragrance materials and essential oils can promote feelings of relaxation and well-being. More recently these materials have been used in cosmetic products to similar effect per se and to enhance the effects of other materials/actives in the products. Many of these products rely on the use of simple mixes of essential oils to provide this benefit, eg lavender, jasmin oil, camomile and ylang-ylang. Many of the materials have been reported to promote different mood states, eg lavender has been reported to be both relaxing (see Torii et al in chapter 7, "Perfumery: the Psychology and Biology of Fragrances", S V Toller and G Dodd (eds), Chapman and Hall, 1991 reprint) and activating (see J S Jellinek, *Perfumer & Flavorist*, vol. 22 (September/October, 29-41). It has therefore been difficult for formulators reliably to use literature information to make effective fragrances. The materials also are not optimised for their acceptability/hedonic effect but are often very basic odour combinations with little of the creativity found in more traditional fragrances.

Aromatherapy employs essential oils which are applied to the skin, for example with massage. The effect here involves additional processes other than smell. However, there are folk remedies in which essential oils are used primarily for their smell and a mood state change may result. In these examples the oils are used singly or in simple mixtures. There is an extensive literature concerning the activities and usage of essential oils for aromatherapy; see for example Tisserand ("The Art of Aromatherapy", C. W. Daniel, London (1985) and "Aromatherapy for Everyone", Penguin Books (1988) both by R. Tisserand). There is also a practice to use the term more freely, for example to claim "aromatherapy products" which may claim to "contain a fragrance which is relaxing and soothing". Consumers are aware that aromatherapy products intend to enhance the sensory experience of the user, but there is no systematic teaching that can direct the perfumer to design products that would consistently provide this benefit. In many cases the claim is more akin to a marketing positioning statement, with a view to differentiating variants or competitive products.

Aroma-Chology® is a term coined by the Olfactory Research Fund Ltd. (see the extensive review by J Jellinek in *Cosmetics & Toiletries*, (1994) 109, pp 83-101). It is concerned specifically with the temporary, beneficial psychological effects of aromas on human behaviours and emotions to improve mood and quality of life. In fact, a large number of products promoted as having aromatherapy benefits can be more accurately identified for their Aroma-Chology® benefits as they produce temporary psychological effects. Again, however, there is no teaching as to how to formulate products to achieve such benefits qualitatively or quantitatively with a reliable expectation of success. In addition it is well known that fragrances can be perceived as associated with different attributes in different countries. Thus it may be that a fragrance found to be "stimulating" to the Japanese consumer will not be "stimulating" to the European consumer. Prior art perfumes do not exhibit the required robustness.

Hirsch (U.S. Pat. No. 5,904,916) teaches a method for enhancing learning in a person by the administration of a mixed/floral odorant, preferably composed of fresh, citrus, herbaceous, fruity and floral odorants, exemplified by Mixed-Floral IFF No. 2635-AS. No further teaching was disclosed on other fragrances of the invention which may have similar psychological benefits.

Clow and Huckelbridge have shown that the smell of chocolate can modulate levels of secretory immunoglobulin A (IgA) which has been linked to stress and mood (see A A Stone et al in *J. Personality and Social Psychology*, (1987), volume 52(5), 988-993). No teachings were provided as to how this might be related to perfume development.

Japanese Patent No. 9-227399 (1997) claims extracts of plants of the Labiatae genus.

Research on the neural basis of emotion has concentrated mostly on fear. The amygdala has been identified as a key component of a network of neural pathways in fear conditioning (see J Le Doux, Annual Review of Psychology, (1995), volume v46, 209) and emotional memories. Many human emotions exist as part of complex neural systems that have evolved to help us survive. Le Doux ("The Emotional Brain: The mysterious Underpinnings of Emotional Life", (1996), publ. Simon & Schuster Inc, New York) points out that emotional responses are hard-wired into the brain's circuitry, and that the stimuli that trigger emotional states are learned through experience. These can be uniformly perceived throughout a population, for example, the sight of a snake triggering a fear response, or of a picture of an injured child eliciting a depressed response. In contrast, the invention described herein identifies a class of perfumes which elicit similarly uniform but pleasant responses. Other fragrances are more susceptible to interpretation being governed by context, eg the country in which the assessor grew up, the appearance of the product in which the perfume is assessed, the use of the product (eg washing with soap).

Kan et al (18th International Congress, IFSCC, Venezia, (October 1994), preprints 769-784) showed that cosmetics which beautify the person have psychoimmunological effects which manifest as an increase in the body's immune status, as measured by salivary IgA. Japanese Patent No. 06172781 describes deactivating (sedative) perfumes based on the use of 1,3-dimethoxybenzene-5-methylbenzene. No teaching on other perfume ingredients was disclosed in either publication.

Alaoui-Ismaili et al (Chem. Senses (1997), 22, 237-248) sought evidence of a linkage between emotion and the sense of smell, particularly smell preference. The results did not provide evidence for the postulated preferential link between olfaction and emotion (although preference scores for their odorants agreed with literature values), leading to the conclusion that the emotional content of smell cannot be predicted from preference. Van Toller et al (*Chemical Senses*, (1993) vol. 18, pp 1-16) found that increased electrical activity (alpha waves) in the brain was associated with increased pleasantness, intensity and familiarity for a range of widely disparate odours.

The present invention seeks to address at least some of the problems described above, in particular that of the creative scope available to perfumers, and possibly also robustness across different consumer groups and performance reliability.

SUMMARY OF INVENTION

The present invention relates to perfume compositions which aim to induce or be associated with positive, low activation moods and emotions. In a first aspect of the invention, a perfume composition comprises:

a) from about 25% in total of at least five Relaxing Ingredients (R);

b) optionally up to 45%, preferably up to 35%, more preferably up to 25%, in total of Non-Relaxing Ingredients (NR), provided that the ratio of R to NR is at least 0.75, preferably at least 0.9;

c) optionally up to 75% in total of Neutral Ingredients (N);

d) optionally up to 25% of other perfumery materials (M) provided that the weight ratio R to (M+NR) exceeds 0.75, preferably 0.9;

and wherein (i) all percentages are based on weight of the perfume composition;
(ii) 'R' ingredients comprise anethole, Bangalol™, basil oil, cis-hex-3-enol, coumarin, ethylene brassylate, ethyl linalol, Florosa™, Galaxolide™, geraniol, cyclohexadecanolide, cyclopentadecanone, methyl anthranilate, alpha-iso-methyl ionone, Prunella™, Silvanone™, alpha-terpineol, Traseolide™, Ultravanil™, gamma-undecalactone, vetiver oil, vetiver acetate;
(iii) 'NR' ingredients comprise methyl nonyl aldehyde (aldehyde MNA), allyl amyl glycolate, acetyl cedrene, Amberlyn Super™, amyl salicylate, armoise oil, benzyl salicylate, bergamot oil, Bourgeonal™, cedar leaf oil, citronellol, beta-damascone, dimethyl benzyl carbinyl acetate, Ethyl Safranate™, Everniate™, geranyl nitrile, Helional™, heliotropin, hexyl salicylate, lemon oil, Ligustral™, Lilial™, Lyral™, Mefrosol™, orange oil, orange terpenes, tagetes oil, tetrahydrogeraniol, vanillin;
(iv) 'N' ingredients comprise benzyl acetate, cassis base, Cyclamen Aldehyde™, carvone, cinnamic alcohol, dihydroeugenol, dihydromyrcenol, eugenol, Extralide™, galbanum, gamma-decalactone, hydroxycitronellal, indole, isoeugenol, jasmin oil, Jasmopyrane Forte™, linalol, linalyl acetate, methyl dihydrojasmonate (MDJ), octahydrocoumarin, patchouli oil, 2-phenylethyl alcohol, rose oxide, rose oil, Sandalone™, Sandalore™, styrallyl acetate, ylang-ylang;
(v) 'M' ingredients comprise perfumery materials not included in the above, excluding odourless or low-odour solvents or diluents used as vehicles for other perfume components.

Another aspect of the invention relates to a method for delivering positive mood benefits, particularly relaxation, to a subject, particularly a human subject, comprising delivering a perfume composition in accordance with the invention in a form selected from consumer products intended for application to skin, hair, hard surface or fabrics, and from air care products such as airfresheners.

The present invention is based on extensive testing of fragrance materials, both by consumer testing and by measurement of brain electrical activity particularly alpha wave activity measured by electroencephalography (EEG), and statistical analysis of the resulting data to classify the materials into different categories, namely relaxing fragrance materials or ingredients (R) that induce in subjects exposed to them positive, low activation moods and emotions, such as relaxation (i.e. relaxing properties), non-relaxing fragrance materials or ingredients (NR) that induce in subjects exposed to them negative, high activation moods or emotions (i.e. non-relaxing properties), neutral fragrance materials or ingredients (N) having a neutral effect in terms of relaxing properties. Other fragrance materials (of which there are around three to four thousand currently available commercially and used in perfume formulation) are designated as class M materials. Based on this classification of fragrance materials, the invention enables perfume compositions to be defined that are likely to induce in subjects exposed to them positive, low activation moods and emotions, such as relaxation. Such perfume compositions are referred to herein for convenience as relaxing perfumes. The definition of the perfume composition nevertheless provides sufficient freedom in formulation to permit consideration of the hedonic properties of the composition. The invention can thus enable formulation of perfume compositions that are relaxing and also have good hedonic properties.

The present invention describes how to formulate reliably novel fragrances which are likely to induce or be associated with positive, low activation moods and emotions, particularly relaxing effects. The effects are sufficiently pronounced that they can be measured reliably and reproducibly. The perfume compositions made according to the teachings disclosed herein can be hedonically pleasant, suitable for a wide range of consumer products, and of sufficient pleasantness/acceptability that they would be appropriate even if they did not possess added functionality. In addition, perfume compositions of the invention can be resilient to variation in the target consumer group (eg Japanese versus American) and have been found to be perceived as consistently relaxing/reassuring etc for consumers in England, France, USA and Japan.

Perfume compositions in accordance with the invention have been found:

a) to promote a reduction in the amplitude of alpha wave activity in the brain;

b) to promote positive mood states such as relaxation. In tests subjects have reported that they feel more relaxed after smelling or using consumer products incorporating the perfume compositions, and subjects report that the products themselves smell more relaxing;

c) to promote calming, warming, sensual, caring, reassuring, safe mood states;

d) not to promote negative mood states such as depressing, stressful, irritating, or bored mood states.

The prior art shows that fragrances which are relaxing (or promote related affect responses) operate by mechanisms other than pleasantness alone. Mood and emotion are hardwired in the brain and are triggered by external stimuli. The basis for systematically selecting olfactory stimuli which evoke specific patterns of brain activity and evoke specific emotions were not previously known. There are a number of methods for gauging the state of relaxation, for example self-appraisal based on adjective-lists, and measurements of brain wave activity, particularly that of the alpha waves (8 to 13 Hz range). In other sensory modalities it would be expected that an increase in power/amplitude in the alpha frequency band would be associated with positive feelings. However, we have found unexpectedly that reduction of odour-derived alpha activity is associated with increased positive feelings and in particular we have found that it is related to positive feelings of less activated mood states (see previous reference for description of positive/negative and activated/deactivated moods and emotions). We have in particular found that reported relaxation is enhanced by fragrances associated with reduced alpha wave activity. We were able to identify fragrance ingredients which are used at higher levels in relaxing fragrances. These were generally materials with notes such as sweet, musky, fruity, floral and amber i.e. unlike the materials disclosed in U.S. Pat. No. 5,904,916 and JP 9-227399 referred to above. Increasing the level of these relaxing ingredients (referred to as class 'R' here) increased the likelihood that the fragrance would have a suitable character to deliver the relaxing benefit. Other ingredients reduce the likelihood that the benefit will be achieved as their level in the fragrance is increased, ie they were the non-relaxing group (referred to as class 'NR' here). A third group had a neutral effect (class 'N'). Combinations of fragrance ingredients which are commercially useful and aesthetically pleasant generally require materials in all three classes to be present. The number of perfume ingredients available commercially is around three to four thousand materials. Surprisingly, these other materials (not in class 'R', 'NR' or 'N' and designated herein as class 'M') may be added to fragrances of the invention without loss of benefit, provided that the weight ratio of relaxing materials to the sum of class M and class NR materials is equal to or greater than around 0.75. In the perfume art, some materials having no odour or very weak odours are used as diluents or vehicles for other ingredients. Non-limiting examples of these are dipropylene glycol (DPG), diethyl phthalate, benzyl benzoate, triethyl citrate and isopropyl myristate. Such materials are not counted towards the definition/formulation of the perfume compositions of the invention.

The present invention thus provides a perfume composition comprising:

(a) at least about 25% by weight in total of at least five relaxing fragrance materials (R);

(b) optionally up to about 45% by weight in total of non-relaxing fragrance materials (NR), provided that the weight ratio of R to NR is at least 0.75;

(c) optionally up to about 75% by weight in total of neutral fragrance materials (N);

(d) optionally up to about 25% by weight of other fragrance materials (M) provided that the weight ratio R to (M+NR) is at least 0.75;

and wherein (i) all percentages are based on total weight of the fragrance materials consisting the perfume composition excluding any solvents and diluents;

(ii) the R materials are selected from the group consisting of anethole, 2-ethyl-4(2',2',3'-trimethylcyclopent-3'-enyl)but-2-enol (eg Bangalol™), basil oil, cis-hex-3-enol, coumarin, ethylene brassylate, ethyl linalol, 2-(2'-methylpropyl)-4-hydroxy-4-methyltetrahydropyran (eg Florosa™), hexahydro-4,6,6,7,8,8-hexamethylcyclopenta[g]-2-benzopyran (eg Galaxolide™), geraniol, cyclohexadecanolide, cyclopentadecanone, methyl anthranilate, alpha-iso-methyl ionone, mixtures of dimethyl benzyl carbinyl butyrate and phenoxyethyl isobutyrate (e.g. Prunella™), mixtures of cyclohexadecanolide and cyclopentadecanone (e.g. Silvanone™), alpha-terpineol, 6-acetyl-1-isopropyl-2,3,3,5-tetrahydrotetralin (eg Traseolide™), 2-ethoxy-4-methylphenol (eg Ultravanil™), gamma-undecalactone, vetiver oil, vetiver acetate;

(iii) the NR materials are selected from the group consisting of methyl nonyl aldehyde, allyl amyl glycolate, acetyl cedrene, 3a,6,6,9a-perhydrotetramethylnaphtho [2,1-b] furan (eg Amberlyn Super™), amyl salicylate, armoise oil, benzyl salicylate, bergamot oil, 4-tert-butyl-3-phenylpropanal (eg Bourgeonal™), cedar leaf oil, citronellol, beta-damascone, dimethyl benzyl carbinyl acetate, ethyl 2,6,6-trimethylcyclohexadienecarboxylate (eg Ethyl Safranate™), methyl 2,4-dihydroxy-3,6-dimethylbenzoate (eg Everniate™), geranyl nitrile, 3-(1,3-benzodioxol-5-yl)-2-methylpropanal (eg Helional™), heliotropin, hexyl salicylate, lemon oil, 2,4-dimethyl-3-cyclohexene-1-carbaldehyde (eg Ligustral™), 3-(4-(1,1-dimethylethyl)phenyl)-2-methylpropanal (eg Lilal™), 4-(4-hydroxy-4-methylpentyl)cyclohex-3-enecarbaldehyde (eg Lyral™), 3-methyl-5-phenylpentanol (eg Mefrosol™), orange oil, orange terpenes, tagetes oil, tetrahydrogeraniol, vanillin;

(iv) the N materials are selected from the group consisting of benzyl acetate, cassis base, 2-methyl-3-(4-(1-methylethyl)phenyl)propanal (eg Cyclamen Aldehyde™), carvone, cinnamic alcohol, dihydroeugenol, dihydromyrcenol, eugenol, 6-acetyl-1,1,3,4,4,6-hexamethyltetrahydronaphthalene (eg Extralide™), galbanum, gamma-decalactone, hydroxycitronellal, indole, isoeugenol, jasmin oil, 3-pentyltetrahydro-2H-4-pyranyl ethanoate (eg Jasmopyrane Forte™), linalol, linalyl acetate, methyl dihydrojasmonate, octahydrocoumarin, patchouli oil, 2-phenylethyl alcohol, rose oxide, rose oil, isobornylcyclohexanol (eg Sandalone™), 5-(2,2,3-trimethyl-3-cyclopentenyl)-3-methylpentan-2-ol (eg Sandalore™), styrallyl acetate, ylang-ylang;

(v) the M materials comprise perfumery materials not included in the above, excluding odourless or low-odour solvents or diluents used as vehicles for fragrance materials.

Preferred perfume compositions comprise at least 35% by weight in total of class R materials, even more preferably at least 45% by weight in total of class R materials. Also preferred are those perfumes wherein the weight ratio of R to NR (or R to the sum of NR and M) exceeds unity, or more preferably exceeds two, or is even higher The perfume composition preferably includes optionally up to about 25% by weight in total of non-relaxing (NR) fragrance materials.

In a particularly preferred embodiment at least 5% by weight, or even more preferably at least 10% by weight, of the perfume composition comprises class R ingredients drawn from the following list, mostly characterised by exhibiting sweet and/or musky notes: coumarin, ethylene brassylate, Galaxolide™, cyclohexadecanolide, cyclopentadecanone, Traseolide™, Ultravanil™, gamma-undecalactone.

The perfume composition may optionally include one or more odourless or low-odour solvents and/or diluents, e.g. as a vehicle for a fragrance material. Any such solvents and/or diluents are not included when calculating percentages and ratios of R, NR, N and M materials of the composition.

It is possible to combine preferred embodiments as defined above to produce fragrances which are highly preferred.

Proprietary Fragrance Materials
Further details on materials are given below.

| Name | Supplier | Technical name/Alternative names * |
|---|---|---|
| Anther ™ | Q | Phenylether isoamyl ether |
| Amberlyn Super ™ | Q | 3a,6,6,9a-perhydrotetramethylnaphtho [2,1-b] furan/Ambrox ™/Cetalox ™ |
| Bangalol ™ | Q | 2-Ethyl-4(2',2',3'-trimethylcyclopent-3'-enyl)but-2-enol |
| Beauvertate ™ | Q | Methyl 2-nonenoate |
| Bourgeonal ™ | Q | 4-tert-butyl-3-phenylpropanal |
| Cyclamen aldehyde ™ | G-R | 2-methyl-3-(4-(1-methylethyl)phenyl)propanal |
| Ethyl safranate ™ | Q | Ethyl 2,6,6-trimethylcyclohexadienecarboxylate |
| Everniate ™ | Q | Methyl 2,4-dihydroxy-3,6-dimethylbenzoate/ Oakmoss synthetic |
| Extralide ™ | Q | 6-Acetyl-1,1,3,4,4,6-hexamethyltetrahydro-naphthalene/Tonalid ™ |
| Florosa ™ | Q | 2-(2'-methylpropyl)-4-hydroxy-4-methyltetrahydropyran |
| Galaxolide ™ | IFF | Hexahydro-4,6,6,7,8,8-hexamethylcyclopenta[g]-2-Benzopyran |
| Indolal | D | 4,5-(1,2-indano)-1,3-dioxan |
| Helional | | 3-(1,3-benzodioxol-5-yl)-2-methylpropanal |
| Heliotropin | | 1,3-benzodioxole-5-carbaldehyde/ Piperonal |
| Iso Ambois ™ | Q | 1-(1,2,3,4,5,6,7,8-Octahydro-2,3,8,8-tetramethyl-2-naphthyl)ethan-1-one/Iso E Super |
| Jasmopyrane Forte ™ | Q | 3-pentyltetrahydro-2H-4-pyranyl ethanoate |
| Ligustral ™ | Q | cis and trans 2,4-dimethyl-3-cyclohexene-1-carbaldehyde |
| Lilial ™ | G-R | 3-(4-(1,1-dimethylethyl)phenyl)-2-methylpropanal |
| Lyral ™ | IFF | 4-(4-hydroxy-4-methylpentyl)cyclohex-3-enecarbaldehyde |
| Mefrosol ™ | Q | 3-methyl-5-phenylpentanol |
| Melonal ™ | G | 2,6-Dimethyl-5-heptenal |
| Ozonal base ™ | Q | complex composition |
| Prunella ™ | F | a mixture of dimethyl benzyl carbinyl butyrate and phenoxyethyl isobutyrate |
| Sandalone ™ | Q | isobornylcyclohexanol |
| Sandalore ™ | G-R | 5-(2,2,3-Trimethyl-3-cyclopentenyl)-3-methylpentan-2-ol |
| Silvanone ™ | Q | Cyclopentadecanone/Cyclohexadecanolide |
| Traseolide ™ | Q | 6-Acetyl-1-isopropyl-2,3,3,5-tetrahydrotetralin |
| Ultravanil ™ | Q | 2-Ethoxy-4-methylphenol |
| Vetiver acetate | IFF | 1,2,3,3a,4,5,6,8a-octahydro-2-isopropylidene-4,8-dimethyl azulen-6-yl acetate |

* Based on major species present in the component.
Suppliers:
D: Dragoco
F: Firmenich
G-R Givaudan-Roure
IFF: International Flavors and Fragrances
Q: Quest International Materials of class 'M' include prior art perfume materials which are not specified as being members of any of classes R, NR or N, excluding odourless or low-odour solvents or diluents, as noted above. They may be single ingredients, or mixtures both synthetic and natural (for example essential oils, and concretes), and are well described e.g. in: "Common Fragrance and Flavor Materials" by Bauer, Garbe and Surburg, VCH Publ., 2nd edition (1990), and "Perfume and Flavour Materials", Steffen Arctander, published in two volumes by the author (1969), and also by Arctander "Perfume and Flavor Materials of Natural Origin", (1960).

Another aspect of the invention relates to a method for delivering positive mood benefits, particularly relaxation, to subjects, particularly humans, comprising delivering fragrance in a form selected from consumer products intended for application to the body (that is to skin or hair), to hard surfaces (eg kitchen and bathroom worktops, ceramic surfaces), to fabrics, and for air care benefits (for example, airfresheners). Such products can take a variety of forms including powders, bars, sticks, tablets, creams, mousses, gels, liquids, sprays, and sheets. The amount of perfume in such products may lie in a range from 0.05% (as for example in low odour skin creams) to 30% (as for example in fine fragrances) by weight thereof. The incorporation of perfume into products of these types is known, and existing techniques may be used for incorporating perfumes for this invention. It may be possible to incorporate perfume directly into a product, but another possibility is, to absorb the perfume on a carrier material and then admix the perfume-plus-carrier mixture into the product.

The invention thus also includes within its scope a consumer product, e.g. a fabric treatment composition, a personal product composition or a hard surface treatment composition, comprising a perfume composition in accordance with the invention.

Also included within the scope of the invention is a method of delivering positive mood benefits or relaxation benefits to a subject, particularly a human, comprising administering to the subject on effective amount of a perfume composition in accordance with the invention. The composition should be administered in appropriate amount to produce a benefit (i.e. a suprathreshold amount) without causing irritation (i.e. a non-irritant amount). An appropriate effective amount of any given composition can be readily determined e.g. by experiment. To be effective, the composition should be administered for inhalation by the subject.

Figure 2:
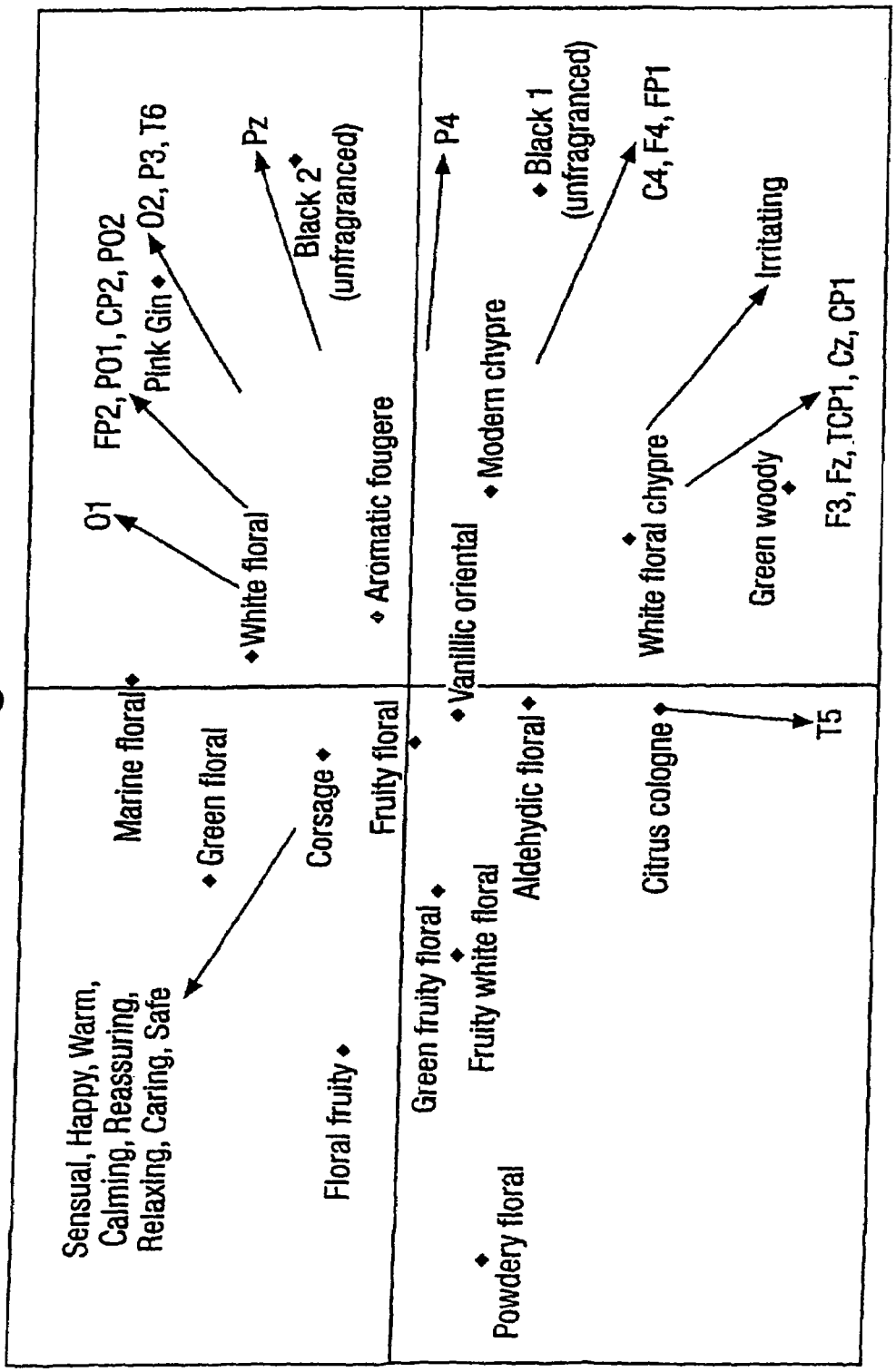

The invention will be further described, by way of illustration, in the following, non-limiting examples. Reference is made to the accompanying drawings, in which:

FIG. 1 is a schematic diagram illustrating electrode placement on the head of a test subject; and FIG. 2 is an example of a map obtained by multidimensional scaling methods (MDS) analysis of brain electrical activity mapping (BEAM) data.

In the Examples, all amounts are expressed as percentages by weight, unless otherwise specified.

EXAMPLES 1-6

Relaxing Perfume Compositions Incorporating Class NR Materials

| | | COMPOSITIONS | | | | | |
|---|---|---|---|---|---|---|---|
| | | w/w % | | | | | |
| INGREDIENT | Class | R1 | R2 | R3 | R4 | R5 | R6 |
| ACETYL CEDRENE | NR | 4.32 | 8.57 | 3.09 | 10.41 | 2.91 | 4.13 |
| ALDEHYDE MNA | NR | 0.04 | 0.02 | 0.03 | 0.04 | 0.03 | 0.03 |

-continued

COMPOSITIONS

| INGREDIENT | Class | R1 | R2 | R3 | R4 | R5 | R6 |
|---|---|---|---|---|---|---|---|
| | | \multicolumn{6}{c}{w/w %} |
| ALLYL AMYL GLYCOLATE | NR | 0.16 | 0.21 | 0.26 | 0.24 | 0.15 | 0.16 |
| AMBERLYN SUPER (Q) | NR | 0.13 | 0.17 | 0.13 | 0.20 | 0.13 | 0.13 |
| AMYL SALICYLATE | NR | 2.53 | 2.20 | 1.88 | 1.76 | 2.44 | 2.43 |
| BANGALOL (Q) | R | 1.15 | 0.73 | 0.42 | 0.64 | 0.43 | 0.76 |
| BEAUVERTATE (Q) | M | 0.00 | 0.00 | 0.00 | 0.44 | 0.00 | 0.00 |
| BENZYL ACETATE | N | 0.92 | 3.75 | 3.06 | 2.44 | 1.91 | 1.67 |
| BENZYL SALICYLATE | NR | 2.65 | 4.60 | 6.04 | 7.68 | 6.61 | 5.95 |
| BOURGEONAL | NR | 0.14 | 0.44 | 0.25 | 0.44 | 0.17 | 0.27 |
| CARVONE | N | 0.11 | 0.10 | 0.10 | 0.14 | 0.10 | 0.11 |
| CINNAMIC ALCOHOL | N | 0.72 | 0.33 | 0.35 | 0.37 | 0.52 | 0.64 |
| CITRONELLOL | NR | 1.04 | 1.53 | 0.93 | 1.41 | 1.65 | 1.35 |
| DIHYDRO MYRCENOL | N | 2.42 | 1.02 | 1.95 | 1.89 | 2.25 | 2.37 |
| ETHYLENE BRASSYLATE | R | 1.31 | 1.70 | 1.19 | 1.45 | 1.13 | 1.26 |
| EXTRALIDE(Q) | N | 0.21 | 0.00 | 0.00 | 0.00 | 0.00 | 0.00 |
| FLOROSA (Q) | R | 9.32 | 10.51 | 11.85 | 9.43 | 2.90 | 8.89 |
| GALBANUM | N | 0.00 | 0.00 | 0.20 | 0.00 | 0.00 | 0.00 |
| HEXYL SALICYLATE | NR | 1.30 | 5.80 | 6.50 | 5.03 | 3.84 | 3.08 |
| ISO AMBOIS (Q) | M | 0.00 | 0.06 | 0.00 | 0.00 | 0.00 | 0.00 |
| JASMIN | N | 0.33 | 0.87 | 0.68 | 0.88 | 0.27 | 0.53 |
| JASMOPYRANE FORTE (Q) | N | 2.50 | 2.47 | 1.51 | 1.87 | 2.30 | 2.33 |
| LIGUSTRAL (Q) | NR | 0.12 | 0.25 | 0.09 | 0.15 | 0.15 | 0.13 |
| LINALOL | N | 2.56 | 1.32 | 6.97 | 3.41 | 1.35 | 2.48 |
| LINALYL ACETATE | N | 3.39 | 4.71 | 4.14 | 5.20 | 2.92 | 3.26 |
| LYRAL (IFF) | NR | 4.18 | 3.19 | 3.72 | 6.40 | 3.73 | 3.78 |
| MDJ | N | 6.66 | 10.95 | 10.24 | 3.97 | 1.67 | 7.48 |
| MEFROSOL (Q) | NR | 2.93 | 5.38 | 7.71 | 4.92 | 4.89 | 3.51 |
| METHYL IONONE ALPHA ISO | R | 19.26 | 6.15 | 4.84 | 6.32 | 1.85 | 12.50 |
| OCTAHYDROCOUMARIN | N | 0.00 | 0.00 | 0.00 | 0.00 | 0.19 | 0.00 |
| ORANGE OIL | NR | 1.40 | 2.76 | 2.47 | 2.60 | 1.46 | 1.46 |
| PHENYL ETHYL ALCOHOL | N | 0.94 | 6.75 | 3.21 | 2.78 | 1.69 | 1.80 |
| SANDALONE(Q) | N | 2.81 | 2.98 | 2.13 | 2.39 | 2.64 | 2.66 |
| SILVANONE (Q) | R | 1.47 | 2.11 | 1.96 | 1.76 | 2.05 | 1.70 |
| TERPINEOL ALPHA | R | 1.45 | 2.16 | 1.88 | 2.07 | 1.67 | 1.62 |
| TRASEOLIDE (Q) | R | 21.26 | 5.95 | 10.09 | 11.08 | 43.83 | 21.11 |
| TUBEROSE BASE | M | 0.00 | 0.00 | 0.00 | 0.00 | 0.00 | 0.21 |
| ULTRAVANIL (Q) | R | 0.01 | 0.01 | 0.00 | 0.00 | 0.01 | 0.01 |
| UNDECALACTONE GAMMA | R | 0.26 | 0.25 | 0.13 | 0.19 | 0.16 | 0.20 |
| total: | | 100.00 | 100.00 | 100.00 | 100.00 | 100.00 | 100.00 |
| sum R | | 55.49 | 29.57 | 32.35 | 32.94 | 54.01 | 48.07 |
| sum NR | | 20.94 | 35.13 | 33.09 | 41.28 | 28.18 | 26.40 |
| sum N | | 23.57 | 35.25 | 34.55 | 25.34 | 17.82 | 25.33 |
| sum M | | 0.00 | 0.06 | 0.00 | 0.44 | 0.00 | 0.21 |
| Ratio R/NR | | 2.65 | 0.84 | 0.98 | 0.80 | 1.92 | 1.82 |
| Ratio R/(M + NR) | | 2.65 | 0.84 | 0.98 | 0.79 | 1.92 | 1.81 |

Notes:
a) Materials marked 'Q' are trademark materials available from Quest International
b) Materials marked 'IFF' are trademark materials available from International Flavors and Fragrances

EXAMPLES 7-8

Comparative Examples of Relaxing (R7) and Non-Relaxing (NR1) Perfume Compositions

| INGREDIENT | Class | R7 (w/w %) | NR1 (w/w %) |
|---|---|---|---|
| ACETYL CEDRENE | NR | 0.00 | 14.58 |
| ALDEHYDE MNA | NR | 0.00 | 0.05 |
| ALLYL AMYL GLYCOLATE (Q) | NR | 0.00 | 0.36 |
| AMBERLYN SUPER PM (Q) | NR | 0.00 | 0.27 |
| BANGALOL (Q) | R | 1.46 | 0.00 |
| BENZYL ACETATE (Q) | N | 5.48 | 6.84 |
| CARVONE LAEVO (Q) | N | 0.15 | 0.18 |
| DIHYDRO MYRCENOL (Q) | N | 4.38 | 5.47 |
| ETHYLENE BRASSYLATE | R | 1.68 | 0.00 |
| FLOROSA | R | 13.14 | 0.00 |
| HYDROXYCITRONELLAL | N | 7.30 | 9.11 |
| JASMIN | N | 0.95 | 1.18 |
| JASMOPYRANE FORTE (Q) | N | 3.94 | 4.92 |
| LIGUSTRAL (Q) | NR | 0.00 | 0.55 |
| LINALOL | N | 7.56 | 9.43 |
| LINALYL ACETATE | N | 5.84 | 7.29 |

-continued

| INGREDIENT | Class | w/w % R7 | w/w % NR1 |
|---|---|---|---|
| LYRAL | NR | 0.00 | 6.84 |
| MDJ | N | 19.43 | 24.27 |
| METHYL IONONE ALPHA ISO | R | 18.25 | 0.00 |
| ORANGE OIL | NR | 0.00 | 2.28 |
| PHENYL ETHYL ALCOHOL | N | 5.11 | 6.38 |
| SILVANONE (Q) | R | 2.92 | 0.00 |
| TERPINEOL ALPHA | R | 2.19 | 0.00 |
| UNDECALACTONE GAMMA | R | 0.22 | 0.00 |
| total: | | 100% | 100% |
| Sum R | | 39.86 | 0.00 |
| Sum NR | | 0.00 | 24.93 |
| Sum N | | 60.14 | 75.07 |
| Sum M | | — | — |
| Ratio R/NR | | — | — |
| Ratio R/(M + NR) | | — | — |

EXAMPLE 9

Relaxing Perfume Composition (R8) Incorporating Significant Proportion of Class M Materials

| Ingredient | Class | w/w % R8 |
|---|---|---|
| ACETYL CEDRENE | NR | 1 |
| ANTHER (Q) | M | 0.4 |
| BANGALOL (Q) | R | 0.4 |
| BEAUVERTATE (Q) | M | 0.3 |
| BENZYL ACETATE | N | 2 |
| BOURGEONAL(Q) | NR | 0.6 |
| CEDAR LEAF OIL (10% in DPG) | NR | 0.6 |
| ETHYL LINALOL | R | 9 |
| ETHYL LINALYL ACETATE | M | 2 |
| ETHYL SAFRANATE (Q) (10% in DPG) | NR | 0.2 |
| FLOROSA (Q) | R | 18 |
| GERANYL NITRILE (10% in DPG) | NR | 0.9 |
| HEXYL CINNAMIC ALDEHYDE | M | 9 |
| INDOLAL (10%) DPG | M | 0.1 |
| JASMOPYRANE FORTE (Q) | N | 1 |
| MEFROSOL (Q) | NR | 4.5 |
| MENTHANYL ACETATE | M | 3 |
| METHYL IONONE ALPHA ISO | R | 4 |
| METHYL ISO EUGENOL | M | 0.3 |
| MOSS OAKMOSS SYNTHETIC (10% in DPG) | NR | 0.2 |
| OZONAL BASE (Q) | M | 0.3 |
| PATCHOULI OIL ACID WASHED | N | 1 |
| PHENYL ETHYL ALCOHOL | N | 4 |
| PARTA-TERT•BUTYL CYCLOHEXYL ACETATE | M | 3 |
| SILVANONE (Q) | R | 4 |
| TERPINEOL ALPHA | R | 3 |
| TETRAHYDROGERANIOL | NR | 1 |
| TRASEOLIDE (Q) | R | 25 |
| ULTRAVANIL (Q) (1% in DPG) | R | 0.7 |
| YLANG-YLANG | N | 0.5 |
| | total | 100 |
| class analysis (excluding solvent) | sum R | 65.22 |
| | sum NR | 7.42 |
| | sum N | 18.64 |
| | sum M | 18.72 |
| | Ratio: R/NR | 8.79 |
| | Ratio: R/(M + NR) | 2.50 |

EXAMPLE 10

Further Embodiments of Perfume Compositions (R9 to R12) in Accordance with the Invention, with Good Hedonic Properties

| INGREDIENT | Class | w/w % R9 | w/w % R10 | w/w % R11 | w/w % R12 |
|---|---|---|---|---|---|
| ACETYL CEDRENE | NR | 4 | 5 | 3.5 | 0 |
| ANETHOLE | R | 0.1 | 0 | 0 | 0 |
| ANISIC ALDEHYDE | M | 0 | 0 | 0.5 | 1 |
| ANTHER | M | 0.8 | 0 | 0 | 0 |
| BANGALOL (Q) | R | 0.5 | 0 | 0.5 | 1.4 |
| BENZYL ACETATE | N | 4 | 0 | 0 | 1 |
| BOURGEONAL (Q) | NR | 0.3 | 0.5 | 0.2 | 0.1 |
| CINNAMIC ALCOHOL | N | 0 | 0 | 0 | 0.8 |
| CIS 3 HEXENOL | R | 0.2 | 0 | 0 | 0 |
| CIS 3 HEXENYL ACETATE | M | 0.2 | 0 | 0 | 0 |
| CITRONELLOL | NR | 0 | 0 | 2 | 1.5 |
| DECALACTONE GAMMA | N | 0 | 0.3 | 0 | 0 |
| DEWFRUIT BASE (Q) | M | 0.1 | 0 | 0 | 0 |
| DIHYDROEUGENOL | N | 0 | 0.3 | 0 | 0.1 |
| DIPROPYLENE GLYCOL | Solv | 6.6 | 25.6 | 10 | 9.6 |
| ETHYL LINALOL | R | 10 | 4 | 1.5 | 0 |
| ETHYL LINALYL ACETATE | M | 5 | 0 | 3.5 | 1 |
| ETHYL SAFRANATE (10% in DPG) | NR/Solv | 0 | 0.2 | 0 | 0.6 |
| ETHYL VANILLIN | M | 0 | 0 | 0 | 0.5 |
| FLOROSA (Q) | R | 15 | 15.2 | 3 | 10 |
| GERANYL NITRILE (10% in DPG) | NR/Solv | 2 | 0.2 | 0 | 0 |
| HELIOTROPIN | NR | 0 | 0 | 0 | 0.9 |
| HEXYL CINNAMIC ALDEHYDE | M | 0 | 5 | 2 | 0 |

-continued

| INGREDIENT | Class | w/w % | | | |
|---|---|---|---|---|---|
| | | R9 | R10 | R11 | R12 |
| HEXYL SALICYLATE | NR | 9 | 0 | 0 | 1 |
| INDOLAL (10% in DPG) | M/Solv | 0.3 | 0.9 | 0 | 0 |
| IONONE | M | 0 | 1.5 | 0 | 0 |
| ISO AMBOIS SUPER (Q) | M | 0 | 0 | 0 | 15 |
| JASMATONE | M | 0.1 | 0 | 0 | 0 |
| JASMOPYRANE FORTE (Q) | N | 2 | 0 | 0 | 0 |
| LIGUSTRAL (Q) | NR | 0.1 | 0 | 0 | 0 |
| MEFROSOL (Q) | NR | 10 | 3 | 6 | 3 |
| MELONAL (10% in DPG) | M | 0 | 0.3 | 0 | 0 |
| METHYL ANTHRANILATE (10% in DPG) | R/Solv | 0.3 | 0 | 0 | 0 |
| METHYL IONONE, alpha iso- | R | 0 | 0 | 2 | 25 |
| MOSS OAKMOSS (10% in DPG) | M | 4 | 0 | 0 | 0 |
| OCTAHYDROCOUMARIN | N | 0 | 0 | 1 | 0 |
| ORANGE TERPENES | NR | 4 | 0 | 0 | 0 |
| OZONAL BASE | M | 0.5 | 6 | 0 | 0 |
| PHENYL ETHYL ALCOHOL | N | 6 | 0 | 2 | 0 |
| PRUNELLA | R | 0 | 0 | 0 | 2 |
| SILVANONE (Q) | R | 0 | 2 | 2.5 | 1.5 |
| TETRAHYDROGERANIOL | NR | 1.5 | 3 | 2.5 | 0 |
| TRASEOLIDE (Q) | R | 12 | 27 | 55 | 23 |
| ULTRAVANIL (1% in DPG) (Q) | R/Solv | 0 | 0 | 1 | 1 |
| UNDECALACTONE GAMMA | R | 0.2 | 0 | 0 | 0 |
| YLANG YLANG | N | 1.2 | 0 | 1.3 | 0 |
| TOTAL | | 100 | 100 | 100 | 100 |
| Class Analysis (excl. solvent) | | | | | |
| | R | 41.76 | 65.82 | 72.48 | 70.79 |
| | NR | 31.96 | 15.76 | 15.95 | 7.38 |
| | N | 14.50 | 0.82 | 4.83 | 2.14 |
| | M | 11.78 | 17.60 | 6.74 | 19.69 |
| | R/NR | 1.31 | 4.18 | 4.54 | 9.59 |
| | R/(NR + M) | 0.95 | 1.97 | 3.19 | 2.61 |

Odour descriptions of the perfume compositions listed above are as follows:

| Composition | Odour Type |
|---|---|
| R1 | Floral fruity |
| R2 | Muguet woody amber |
| R3 | Green fruity floral |
| R4 | Green floral |
| R5 | Powdery floral |
| R6 | Fruity floral |
| R7 | Muguet violet sandalwood |
| R8 | Fruity floral |
| R9 | Green fruity floral |
| R10 | Marine floral |
| R11 | Powdery floral |
| R12 | Floral fruity |

EXAMPLES 11-12

Mood Data

Example 11

Methodology

The moods elicited by different fragrances were investigated using naïve consumers. Each subject assessed each of the test fragrances, presented blind and in a balance randomised order. The method used was line-scaling. In this method a mark is placed on a line at a point between the two ends which represents the relative similarity/difference between the properties of the sample and the adjectives associated with each end of the line. The instructions given were "Please put a mark on each line listed to indicate how you feel about the odour". This was followed by a list of the attributes, shown below, each with a line scale as illustrated. The data were analysed using standard statistical methods, see below.

The characteristics assessed were as follows:

| | |
|---|---|
| Trendy | Calming |
| Nostalgic | Relaxing |
| Warm | Comforting |
| Simulating | Happy |
| Modern | Irritating |
| Sensual | Depressing |
| Stressful | Invigorating |
| Soothing | Cooling |
| Refreshing | Sexy |
| Safe | Reassuring |
| Caring | Liking |

Example of Line Scale

| CALMING |
|---|
| Extremely ...................X.................. Not at all |

The data was analysed by Analysis of Variance (ANOVA) to generate mean scores which were used for further analysis.

| Fragrance | Sum of 'Relaxation' scores** | Effect |
|---|---|---|
| R1 | 80 | Highly Relaxing |
| R2 | 62 | Relaxing |
| R3 | 59 | Relaxing |
| R4 | 53 | Relaxing |
| R5 | 77 | Highly Relaxing |
| R6 | 66 | Relaxing |
| R7 | 85 | Highly Relaxing |
| R8 | 75 | Highly Relaxing |
| NR1 | 25 | Non-Relaxing |
| 2635-AS* | 50 | Relaxing |

*Prior art fragrance in U.S. Pat. No. 5,904,916
**estimates

Example 12

Methodology

The moods elicited by different fragrances were investigated using naïve consumers. Each subject assessed each of the test fragrances, presented blind and in a balance randomised order. The method used was line-scaling. In this method a mark is placed on a line at a point between the two ends which represents the relative similarity/difference between the properties of the sample and the adjectives associated with each end of the line. The instructions given were "Please put a mark on each line listed to indicate how the product makes you feel". The characteristics used were as follows:

| | |
|---|---|
| Trendy | Calm |
| Nostalgic | Warm |
| Stimulated | Modern |
| Sensual | Stressed |
| Soothed | Refreshed |
| Safe | Cared for |
| Relaxed | Comfortable |
| Happy | Irritated |
| Depressed | Invigorated |
| Sexy | Reassured |

Note: descriptors should be understandable and relevant to local tastes and understanding. Words such as 'cool; can be ambiguous when used internationally.

| Fragrance | Sum of 'Relaxation' scores** | Effect |
|---|---|---|
| R1 | 75 | Highly Relaxing |
| R2 | 66 | Relaxing |
| R3 | 61 | Relaxing |
| R4 | 50 | Relaxing |
| R5 | 71 | Highly Relaxing |
| R6 | 67 | Relaxing |
| R7 | 78 | Highly Relaxing |
| R8 | 71 | Highly Relaxing |
| NR1 | 29 | Non-Relaxing |
| 2635-AS* | 46 | Relaxing |

*Prior art fragrance in U.S. Pat. No. 5,904,916
**estimates

EXAMPLE 13

Spontaneous Cortical Activity in Response to a Range of Fragrances and Interpretation of This Response in Consumer Terms It is well recognised that odours can elicit powerful emotional responses and recall vivid memories. In an attempt better to understand the linkage between odour and emotion researchers have tried to understand the workings of the brain itself. Much has been made of the organisation of the olfactory structures linked directly into the limbic system which itself has been traditionally linked to emotion. However until recently there has been a lack of understanding of brain mechanisms and there has been difficulty in detecting and localising brain activity.

Development of Brain Electrical Activity Mapping (BEAM) by the inventors has involved testing of a wide range of odour types. We have identified significant differences in patterns of brain activity recorded from the surface of the scalp in response to the different odour stimuli. A key question is whether these different patterns of brain activity could give an indication of how people feel in response to fragrance. This was researched by testing a wide range of fragrance types both for patterns of brain activity (using BEAM techniques) and through large scale consumer surveys carried out in the US, France and Germany. The different data sets were compared and correlations were found.

Brain Electrical Activity Mapping

This technique enables measurement of changes in patterns of brain response in real time. The experiment was conducted in a large well ventilated laboratory with the subjects seated comfortably in an armchair. During the experiment subjects experienced reduced visual and auditory perception. To achieve this subjects wore blacked out goggles and headphones which gave a tolerable level of white noise about (70 dB). The headphones also allowed the experimenter to communicate with subjects between electroencephalograph (EEG) recording trials. All subjects reported afterwards that they found the experiment to be relaxing and pleasant.

EEG data were collected from over the whole of the scalp using a fabric cap which contained 28 electrodes (Electro-cap International, Inc., USA) built into small plastic buttons in an enhanced International 10/20 electrode placement system. The electrodes were made from highly purified tin and referenced to linked earlobes. A NaCl/KCl gel was used as the conducting medium. The configuration over the scalp is given in FIG. 1. Bandpass filters were set at 0.3 and 40 Hz. And sampling rate was 200 Hz. The data handling system dealt with amplitude data from each of the 28 electrodes for all of the conventional EEG wavebands.

A Neuroscience Brain Imager series III model was used to collect the EEG data. This machine uses a computerized real time Fast Fourier Transformation (FFT) technique which allows the averaging of the EEG responses over 2.56 second periods or frames. The EEG signals recorded from the subject are amplified, filtered and then multiplexed prior to analogue to digital conversion. The Neuroscience Imager gives an averaged EEG amplitude for each electrode shown in FIG. 1 every 2.56 s.

EEG data were collected from all of the classical frequency bands (delta, 0-3.5 Hz; theta, 4-7 Hz; alpha 8-13 Hz; beta 1, 15-30 Hz and beta 2 31+ Hz). It was found, in line with earlier similar investigations (e.g. Van Toller et al 1993 (S van Toller, J Behan, P Howells, M Kendal-Reed and A Richardson, "An analysis of spontaneous human cortical EEG activity to odours", Chemical Senses, vol. 18, pages 1-16 (1993)), and Moncrief 1962 (R Moncrieff, "Effects of odours on EEG records", Perfumery Essential Oil Rec., vol. 53, pages 757-760 (1962)) that the predominant change in activity on presentation of the odours was located in the alpha EEG frequency (8-13 Hz). For each electrode a mean amplitude value for the alpha frequencies was calculated across subjects for the first 2.56 second epoch after each stimulus presentation. These means were used to derive a quantitative measure of similarity of EEG responses which were used as input for multivariate analysis eg using Multidimensional Scaling methods (MDS).

Data Analysis

To analyse the data we followed the approach described by Schiffman (see S Schiffman, M Reynolds and F Young, "Introduction to Multidimensional Scaling", Academic Press (1981), and also J Behan and A Richardson, "Sensory Analysis in the Fragrance Industry", Cosmetics & Toiletries, 35-39 (1990)). The stimulus space (or map) was derived from a multidimensional scaling (MDS) analysis of the BEAM data. An example of a graphical plot with points for each fragrance given as FIG. 2. The contributions of activity at different locations on the scalp was analysed by fitting averaged data for each electrode to the MDS configuration using a vector correlation model (ie the electrode contributions are shown by arrows with the electrode label, O1, FP2, etc, in FIG. 2). The same technique was then also used to relate market research data on the fragrance stimuli to the same MDS-derived space (shown as as an arrow in the top left hand corner eg 'sensual', 'happy', and in the bottom right hand corner for 'irritating'). By inspection it is possible to deduce the relationship of the various dimensions of response to each other, in particular the relationship between the market research data and the changes in brain wave activity following exposure to perfume.

The MDS map in this case is based on the similarity/dissimilarity of brain response patterns for each perfume. The more different the brain response patterns arising from two of the fragrances, the further apart the two fragrances will appear on the MDS map. The vector model finds the best correlation between the two data sets (ie between the MDS space and the amplitude of response recorded at the electrodes, or between the MDS space and each market research attribute).

Results

Typical BEAM electrode data (in microvolts) are shown in Table 1 for fragrances R2 and R4

The importance of each electrode/attribute to the interpretation of the MDS configuration was determined using formal statistical tests based on F ratios for the vector preference model, as described in the Schiffman reference above. Such an analysis revealed for example that the electrodes Oz, C3, F7, T3, FTC1, F8, T4, FTC2, TCP2 did not meet the set criterion for significance and thus these have not been considered further.

The MDS map was also examined using consumer mood profiling research data, and significant common attributes were identified for the countries where testing was conducted. A summary chart bringing the different facets together is shown in FIG. 2 with correlations with German market research data. For the German market research nine of the attributes can be described by the vector model with F-ratios significant at the 5% level. The vectors are shown on the map in FIG. 2, pointing in the direction of increasing perception. Maps (not shown) for US and French data were very similar.

CONCLUSIONS

By referring to the map shown in FIG. 2 and by referring to the related correlation statistics described above we can infer that for this set of fragrances the direction of increasing perception of sensual, happy, warm, calming, safe, reassuring, relaxing and caring across the stimulus space is related to a decrease in activity on electrodes CP1, FP1, C4, F4, TCP1, F3, Fz, and Cz. In view of the wide range of fragrance types studied, the large population of people included in the consumer research, and similar trends observed in additional studies we have concluded that this is a general trend that can safely be applied to other fragrance sets within a similar odour world.

This and a large amount of other similar data was used to classify fragrance ingredients as R, NR and N, as discussed above, providing the information on which the invention is based.

TABLE 1

| Electrode data | | |
|---|---|---|
| Electrode | R2 | R4 |
| 1 (FP1) | 13 | 11 |
| 2 (Fz) | 14 | 13 |
| 3 (Cz) | 14 | 13 |
| 4 (Pz) | 20 | 23 |
| 5 (Oz) | 14 | 15 |
| 6 (F3) | 11 | 13 |
| 7 (C3) | 11 | 10 |
| 8 (P3) | 17 | 13 |
| 9 (O1) | 13 | 11 |
| 10 (F7) | 10 | 10 |
| 11 (T3) | 8 | 9 |
| 12 (T5) | 12 | 12 |
| 13 (FTC1) | 11 | 13 |
| 14 (TCP1) | 12 | 12 |
| 15 (CP1) | 16 | 14 |
| 16 (PO1) | 18 | 15 |
| 17 (FP2) | 13 | 12 |
| 18 (F4) | 14 | 16 |
| 19 (C4) | 11 | 9 |
| 20 (P4) | 14 | 13 |
| 21 (O2) | 10 | 11 |
| 22 (F8) | 9 | 8 |
| 23 (T4) | 11 | 8 |
| 24 (T6) | 13 | 9 |
| 25 (FTC2) | 10 | 9 |
| 26 (TCP2) | 9 | 11 |
| 27 (CP2) | 8 | 9 |
| 28 (PO2) | 15 | 14 |

The invention claimed is:

1. A method of producing a relaxed mood in a subject in need of same, said method comprising administering to the subject an effective amount of a perfume composition comprising:
   a) from about 25% in total of at least five Relaxing Ingredients (R);
   b) some up to 25% in total of Non-Relaxing Ingredients (NR), provided that the ratio of R to NR is at least 0.9;
   c) some up to 75% in total of Neutral Ingredients (N);
   d) some up to 25% of other perfumery materials (M) provided that the weight ratio R to (M+NR) exceeds 0.9;
   and wherein
      (i) all percentages are based on weight of the perfume;
      (ii) 'R' ingredients selected from the group consisting of anethole, 2-ethyl-4(2',2',3'-trimethylcyclopent-3'-enyl)but-2-enol, basil oil, cis-hex-3-enol, coumarin, ethylene brassylate, ethyl linalol, 2-(2'-methylpropyl)-4-hydroxy-4-methyltetrahydropyran, hexahydro-4,6,6,7,8,8-hexamethylcyclopenta[g]-2-benzopyran, geraniol, cyclohexadecanolide, cyclopentadecanone, methyl anthranilate, alpha-iso-methyl ionone, alpha-terpineol, 6-acetyl-1-isopropyl-2,3,3,5-tetrahydrotetralin, 2-ethoxy-4-methjylphenol, gamma-undecalactone, vetiver oil, and vetiver acetate;

(iii) 'NR' ingredients selected from the group consisting of methyl nonyl aldehyde, allyl amyl glycolate, acetyl cedrene, 3a,6,6,9a-perhydrotetramethylnaphtho[2,1-b]furan, amyl salicylate, armoise oil, benzyl salicylate, bergamot oil, 4-tert-butyl-3-phenylpropanal, cedar leaf oil, citronellol, beta-damascone, dimethyl benzyl carbinyl acetate, ethyl 2,6,6-trimethylcyclo-hexadienecarboxylate, methyl 2,4-dihydroxy-3,6-dimethylbenzoate, geranyl nitrile, 3-(1,3-benzodioxol-5-yl)-2-methylpropanal, heliotropin, hexy salicylate, lemon oil, 2,4-dimethyl-3-cyclohexene-1-carbaldehyde, 3-(4-(1,1-dimethylethyl)phenyl)-2-methylpropanal, 4-(4-hydroxy-4-methylpentyl)cyclohex-3-enecarbaldehyde, 3-methyl-5-phenylpentanol, orange oil, orange terpenes, tagetes oil, tetrahydrogeraniol, and vanillin;

(iv) 'N' ingredients selected from the group consisting of benzyl acetate, cassis base, 2-methyl-3-(4-(1-methylethyl)phenyl)propanal, carvone, dihydroeugenol, dihydromyrcenol, eugenol, 6-acetyl-1,1,3,4,4,6-hexamethyltetrahydronaphthalene, gamma-decalactone, hydroxycitronellal, indole, isoeugenol, jasmin oil, 3-pentyltetrahydro-2H-4-pyranyl ethanoate, linalol, linalyl acetate, methyl dihydrojasmonate, octahydrocoumarin, patchouli oil, 2-phenylethyl alcohol, rose oxide, rose oil, isobornylcyclohexanol, 5-(2,2,3-trimethyl-3-cyclopentenyl)-3-methylpentan-2-ol, styrallyl acetate and, ylang-ylang;

(v) 'M' ingredients selected from the group consisting of perfumery materials not included in the above, excluding odourless or low odour solvents or diluents used as vehicles for fragrance components.

* * * * *